(12) United States Patent
Fujita

(10) Patent No.: US 6,408,701 B1
(45) Date of Patent: Jun. 25, 2002

(54) APPARATUS FOR MEASURING CONTAMINATION OF THE SURFACE OF A MACHINE SURFACE

(75) Inventor: Ikuhiro Fujita, Kumamoto (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/567,642

(22) Filed: May 9, 2000

(30) Foreign Application Priority Data

May 12, 1999 (JP) .......................................... 11-131585

(51) Int. Cl.[7] .................................................. G01N 1/04
(52) U.S. Cl. .................................. 73/864.71; 73/864.33
(58) Field of Search ........................ 73/863.23, 864.33, 73/864.34, 864.71, 864.81

(56) References Cited

U.S. PATENT DOCUMENTS

| | | | | |
|---|---|---|---|---|
| 3,362,141 A | * | 1/1968 | Royster, Jr. et al. | 73/864.33 |
| 5,211,062 A | * | 5/1993 | Moser | 73/864.33 |
| 5,503,005 A | * | 4/1996 | Carlton | 73/866 |
| 5,783,938 A | * | 7/1998 | Munson et al. | 73/864.33 |
| 5,939,647 A | * | 8/1999 | Chinn et al. | 73/864.71 |
| 6,193,482 B1 | * | 2/2001 | Chen | |

FOREIGN PATENT DOCUMENTS

| | | | | |
|---|---|---|---|---|
| GB | 2088055 | * | 6/1982 | 73/864.35 |
| JP | 10-10018 | | 1/1998 | |

* cited by examiner

Primary Examiner—Robert Raevis
(74) Attorney, Agent, or Firm—Hutchins, Wheeler & Dittmar

(57) ABSTRACT

A surface contamination measuring apparatus has a suction means for sucking in air from the proximity of an object under measurement, a measurement section for measuring the amount and composition of sucked-in particles, a discharging means for discharging a fluid onto the surface of the object under measurement, a sampling member brought into proximity to surface of the object under measurement, and a blocking member made of a flexible member at the periphery of the sampling member, and can efficiently capture particles that has become attached to the surface under measurement.

9 Claims, 5 Drawing Sheets

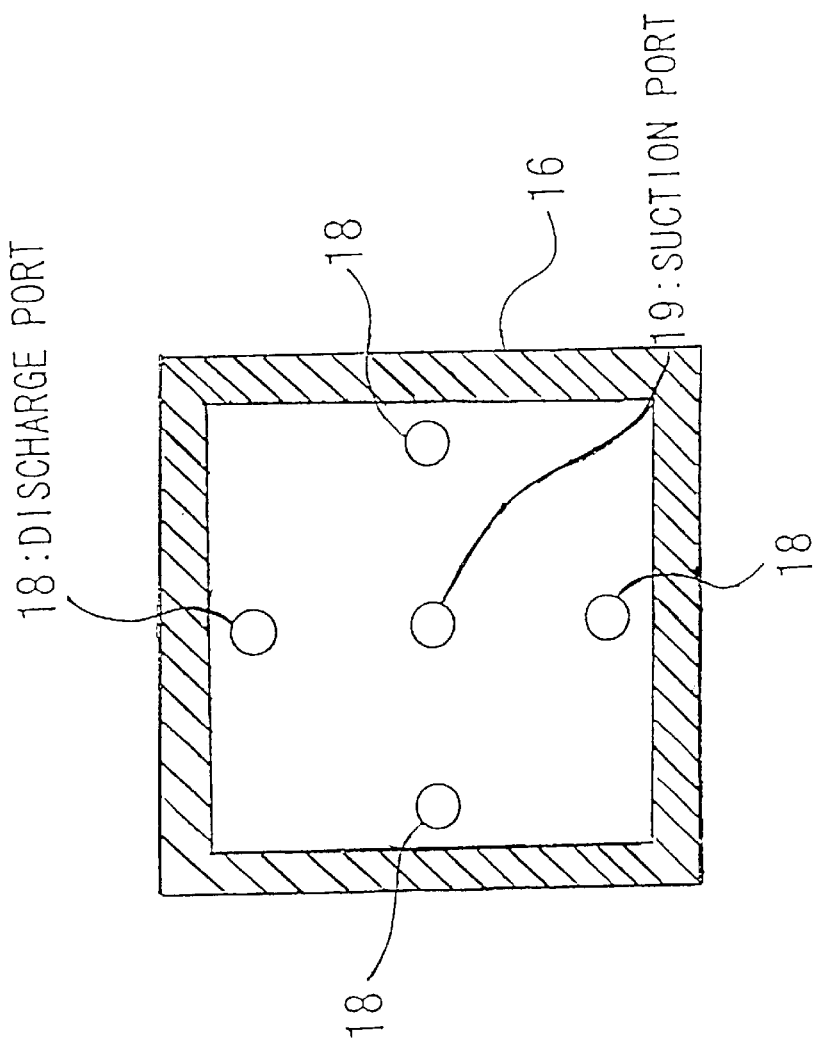

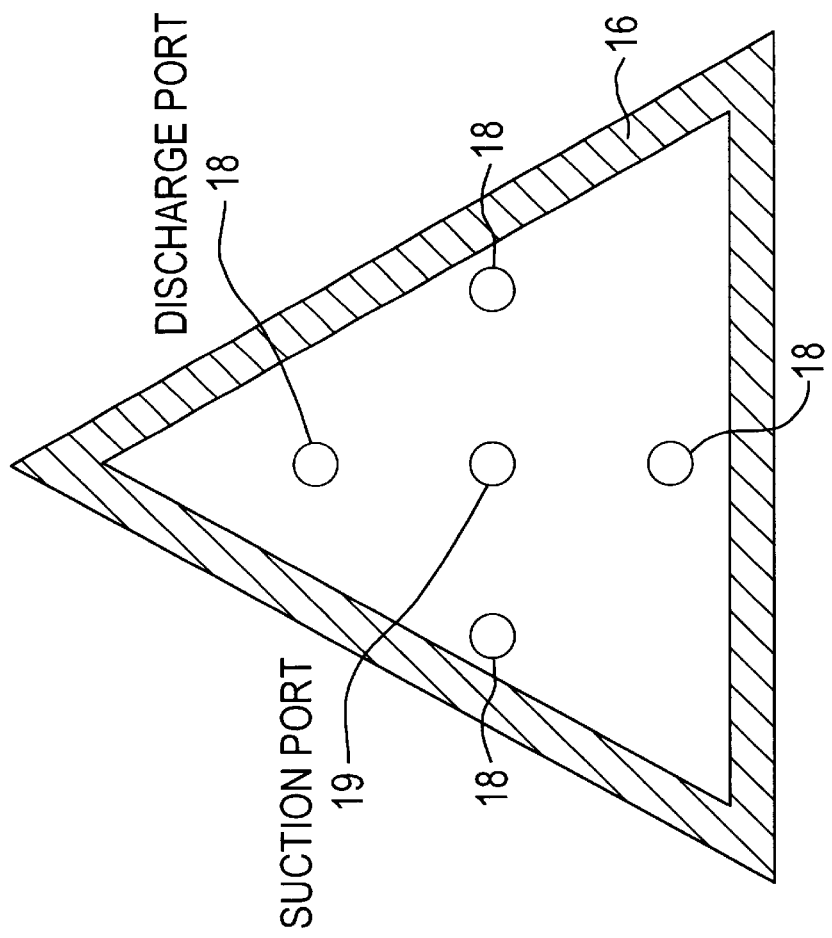

APPARATUS FOR MEASURING CONTAMINATION OF THE SURFACE OF A MACHINE SURFACE

BACKGROUND OF THE INVENTION

1. Field of the Invention

The present invention relates :to a surface contamination measuring apparatus for capturing particles that have become attached to a semiconductor wafer surface, to a liquid crystal glass, to a chip, or to the surface of a semiconductor device or manufacturing apparatus therefore, which is used to analyze the cause of the contamination.

2. Description of the Related Art

In general, an apparatus for measuring surface contamination in the past, as shown in FIG. 6 had a suction nozzle 6 disposed in the area around a spray nozzle 5, whereby a particle 8 that has become attached to the surface under measurement is first picked up by air from the spray nozzle 5, and then captured by a suction nozzle 6. The captured particles 8 are collected on a filter (not shown in the drawing), and an analysis is made of the cause of the contamination.

In the above-noted surface contamination measuring apparatus, however, the following problems existed.

For example, in the system illustrated in FIG. 6, because a large amount of air is taken in from the area surrounding the suction nozzle 6, it was not possible to efficiency suck in the particles 8 that have become attached to the surface under measurement.

Additionally, when a nozzle is brought into proximity with the surface under measurement, although the suction force is increased, it becomes difficult to control the gap with respect to a semiconductor wafer, for example.

This type of surface contamination measuring apparatus is disclosed in the Japanese Unexamined Patent Application publication H10-10018, for example. This type of surface contamination measuring apparatus, results in a large amount of air being taken in from the area surrounding the suction nozzle 6, making it impossible to efficiency suck in a particle 8 that has become attached to the surface under measurement.

Accordingly, it is an object of the present invention to improve on the above-noted drawbacks in the prior art, by providing a surface contamination measuring apparatus which can measure particles on the surface under measurement, with good efficiency, and without requiring difficult control of a gap.

SUMMARY OF THE INVENTION

In order to achieve the above-noted object, the present invention has the following technical constitution.

A first aspect of the present invention has a suction means for taking in air from the proximity of the object under measurement, a measurement section for measuring the amount of, or composition of particles in the sucked in air, a discharging means for discharging a fluid onto the surface of the object under measurement, and a sampling member, which is caused to come into proximity with the surface of the object under measurement, wherein a flexible blocking member being provided on a circumference portion of the sampling member.

In order to solve the problems of the prior art, a surface contamination measuring apparatus according to the present invention has a suction means for taking in air from the surface of the object under measurement, a measurement section for measuring a number of the particles in the sucked in air, a discharging means for discharging a fluid onto the surface of the object under measurement, and a sampling member mounted to the surface of the object under measurement, and isolates the area surrounding the sampling member from the outside by a flexible blocking member, thereby enabling the efficient capture of particles.

BRIEF DESCRIPTIONS OF THE DRAWINGS

FIG. 7 is a bottom plan view showing a sampling member of the surface contamination measuring apparatus in accordance with an alternate embodiment.

FIG. 8 is a bottom plan view showing a sampling member of the surface contamination measuring apparatus in accordance with yet another alternate embodiment.

DETAILED DESCRIPTION OF THE PREFERRED EMBODIMENTS

Embodiments of the present invention are described in detail below, with reference made to relevant accompanying drawings.

Figure 1:
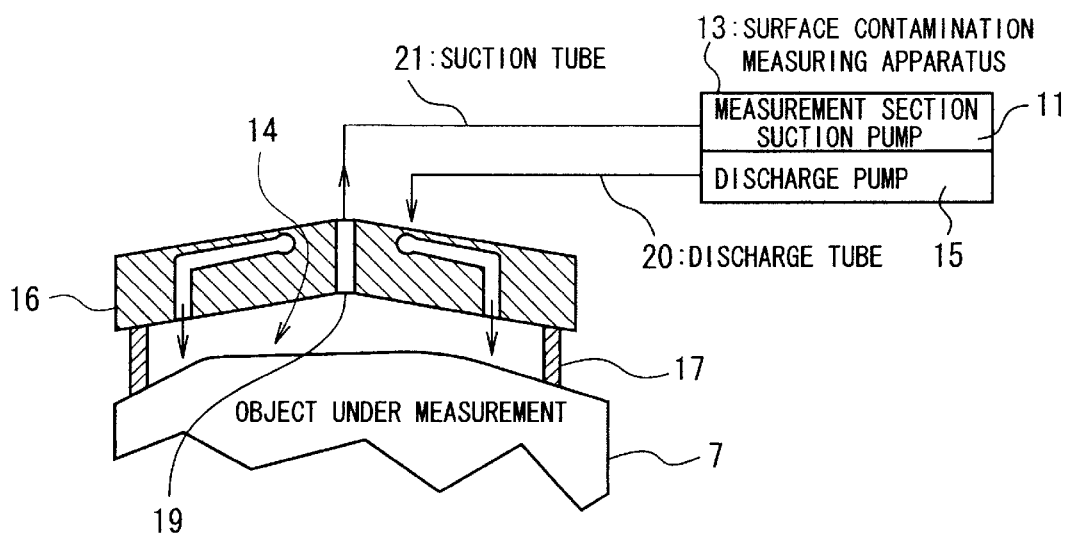
FIG. 1 is a drawing showing the overall configuration of a surface contamination measuring apparatus according to an embodiment of the present invention.
Figure 2:
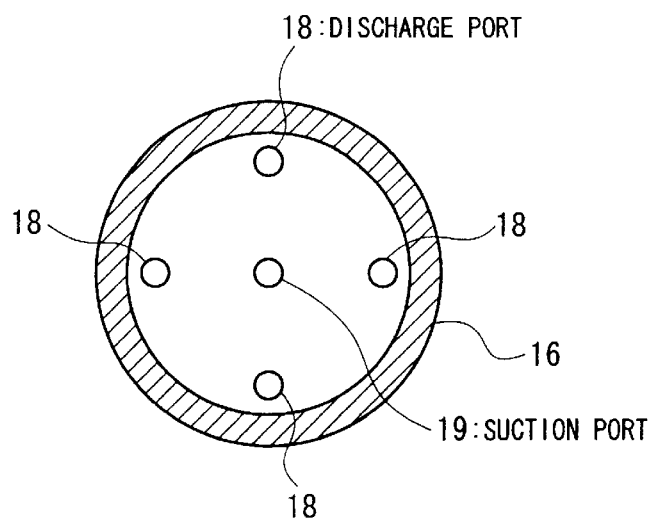
FIG. 2 is a bottom plan view showing a sampling member of the surface contamination measuring apparatus of FIG. 1.
Figure 3:
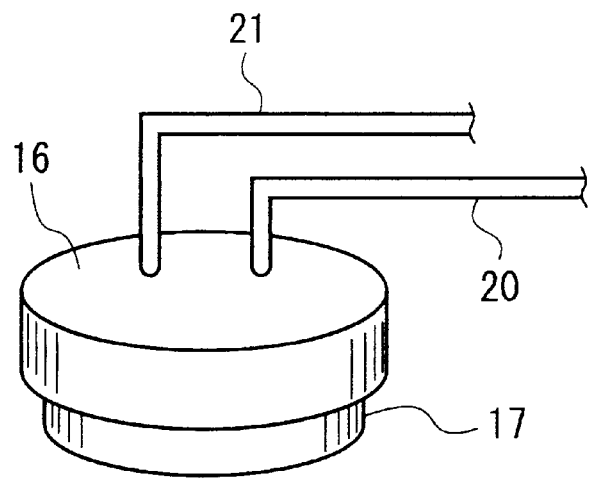
FIG. 3 is a perspective view showing the sampling member of the surface contamination measuring apparatus of FIG. 1.

FIG. 1 shows the overall configuration of an apparatus surface contamination measuring apparatus, which is the first embodiment of the present invention, FIG. 2 is a bottom plan view of the sampling member in the apparatus of FIG. 1, and FIG. 3 is a perspective view showing the sampling member of the same apparatus of FIG. 1.

The apparatus surface contamination measuring apparatus 10 has a suction pump 11 serving as a suction means for sucking in air from the proximity of the object under measurement, a measurement section 13 for measuring, for example, an amount of composition, of particles in the sucked in air, a discharge pump 15 serving as a discharging means for discharging a fluid onto the surface of the object under measurement, a sampling member 16 that is brought into proximity with the surface of the object under measurement, and a flexible blocking member 17 covering the area surrounding the sampling member 16.

The apparatus surface contamination measuring apparatus 10 has a suction pump 11 and a discharge pump 15, a suction tube 21 provided so as to extend from the suction pump 11 communicating with a suction port 19 of the sampling member 16. In the first embodiment, the suction port 19 is opened up in substantially the center of a round sampling member 16.

A particle 12 that is sucked in from the suction port 19, is transported to the measurement section 13 via the suction tube 21, at which it is captured by a filter or the like, the captured particle being measured for elemental composition, for example, element analysis measuring device.

A discharge tube 20 connected to the discharge pump 15 communicates with a discharge port 18 of the sampling member 16. The discharge port 18, as shown in FIG. 2 is disposed in the area surrounding the suction port 19. The surface of the sampling member 16 opposing the object under measurement 7 has a flexible member 17 which is continuously provided along a peripheral portion of the sampling member 16. The flexible member 17 is made of soft rubbery material and is mounted along the outer periphery with a height from several millimeters to approximately 1 centimeter. The flexible member 17 in this embodiment is made of a single sheet of rubber or the like, and it serves as a blocking member.

The method of using the apparatus surface contamination measuring apparatus configured as noted above is as follows. The measurement procedure is one of first bringing the sampling member 16 into contact with a surface of the object 14 under measurement so that there is no gap therebetween. Next, a minute amount of air is discharged on the surface of the object under measurement from the discharge port 18 via the discharge pump 15 and discharge tube 20.

The air from the discharge port 18 causes a particle that has become attached to the surface under measurement 14 to jump up, whereupon it is sucked into the suction port 19. The sucked in particle passes through the suction tube 21 and is transported to the measurement section 13.

When this occurs, the area surrounding the sampling member 16 is covered with the flexible member 17, making it possible to suck in a measure the atmosphere between the surface 14 under measurement and the sampling member 16. Therefore, because air is not sucked in from the outside, it is possible to suck in only the particles of the surface under measurement 14. Because the area surrounding the sampling member 16 is covered by the flexible member 17, it is possible to cause a particle to jump up by the action of the minute amount of air from the discharge port 18.

Figure 4:
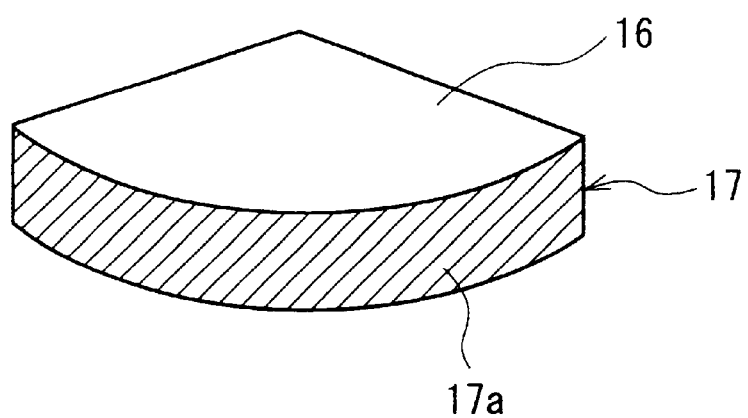
FIG. 4 is a perspective view showing another embodiment of a sampling member of the surface contamination measuring apparatus.

Next, referring to FIG. 4, which shows a perspective view of another embodiment of a sampling member in an apparatus surface contamination apparatus according to the present invention, in this embodiment, the flexible member 17 has formed on it a plurality of overlapping narrow, thin rectangular pieces 17a. That is, the narrow rectangular pieces 17a are disposed so as to be partially overlapped with adjacent pieces.

In the above-noted configuration, the space between the surface under measurement 14 and the sampling member 16 is covered from the outside, enabling efficient suction of particles. Because the flexible member 17 can freely deform, it is possible to suck in particles, even if the surface under measurement is spherical or otherwise vertically uneven.

By adjusting the shape of the sampling member 16 itself to the shape of the surface under measurement 14, it is possible to freely accommodate rectangular, triangular, and segment shapes or the like.

Figure 5:
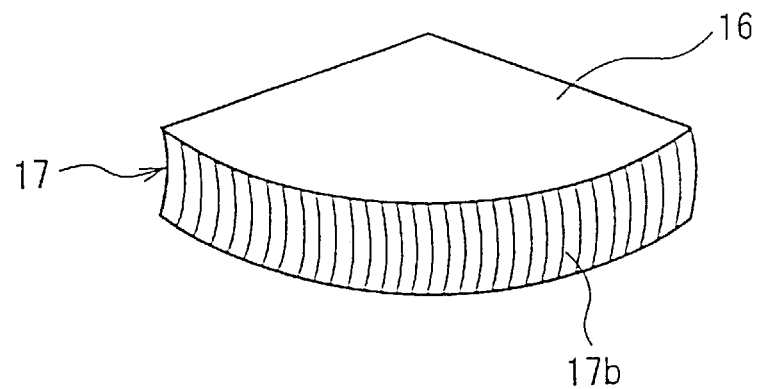
FIG. 5 is a perspective view showing a third embodiment of a sampling member of a surface contamination measuring apparatus.
Figure 6:
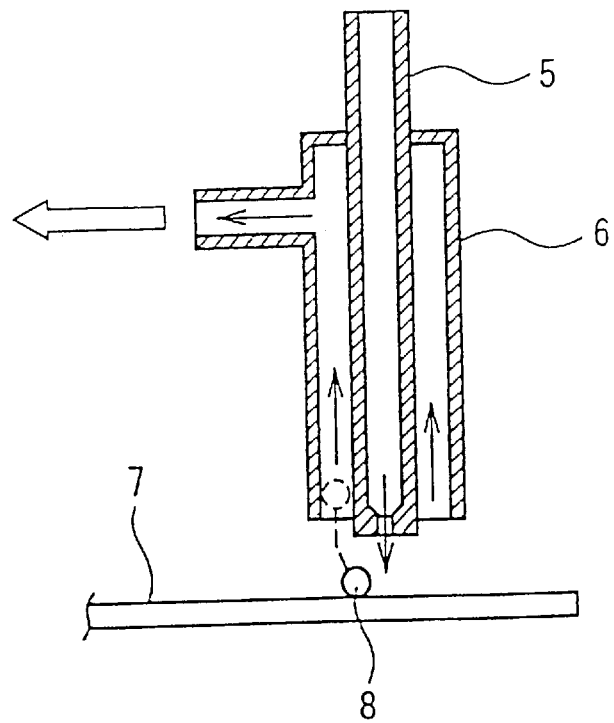
FIG. 6 is a drawing showing a prior art configuration of a surface contamination measuring apparatus.

FIG. 5 is a perspective view showing a third embodiment of a sampling member 16 of an apparatus surface contamination measuring apparatus according to the present invention. In this embodiment, the flexible member 17 has narrow rubber pieces 17b mounted as brushes around the outer periphery of the sampling member 16.

In the above-noted configuration, it is possible to achieve an intimate seal between the surface under measurement 14 and the sampling member 16. It is therefore possible with only a minute amount of discharged air to cause particles to jump up and suck in the particles.

It will be understood that the present invention is not restricted to the exemplary embodiments described above, but can take on other variations, within the spirit and scope of the underlying technical concept thereof.

As described in detail above, one effect achieved by an apparatus surface contamination measuring apparatus according to the present invention is that, even in the case of a spherical or otherwise uneven surface under measurement, it is possible to efficiently suck in particles from the surface, without a gap occurring between the sampling member and the surface under measurement.

Additionally, because there is an intimate seal developed at the gap between the surface under measurement and the sampling member, it is possible to effectively cause particles attached to the surface to jump up with a minute amount of air.

Additionally, because there is an intimate seal developed at the gap between the surface under measurement and the sampling member, it is possible to effectively capture particles that have jumped up, without allowing them to escape.

What is claimed is:

1. A surface contamination measuring apparatus comprising:

means for sucking in air from the proximity of an object under measurement;

a measurement section for measuring one of a quantity of, and a composition of, particles in the sucked in air;

a discharging means for discharging a fluid onto a surface of said object under measurement;

a sampling member brought into proximity with a surface of said object under measurement and connected to the means for sucking in air and the discharging means of discharging a fluid; and a blocking member made of a flexible material being provided at about the outer periphery of said sampling member, wherein said flexible material comprises a plurality of separate individual members each having substantially rectangular shapes, and disposed continuously so that a part of each individual one thereof overlaps with another.

2. A surface contamination measuring apparatus comprising:

means for sucking in air from the proximity of an object under measurement;

a measurement section for measuring one of a quantity of, and a composition of, particles in the sucked in air;

a discharging means for discharging a fluid onto a surface of said object under measurement a sampling member brought into proximity with a surface of said object under measurement and connected to the means for sucking in air and the discharging means of discharging a fluid; and a blocking member made of a flexible material being provided at about the outer periphery of said sampling member, wherein said flexible material comprises a plurality of separate individual substantially vertical elements disposed continuously around a circumference of the sampling member and disposed to conformally contact the surface of the object to be measured with a substantially light contact as brushes.

3. A surface contamination measuring apparatus comprising:

means for sucking in air from the proximity of an object under measurement;

a measurement section for measuring one of a quantity of, and a composition of, particles in the sucked in air;

a discharging means for discharging a fluid onto a surface of said object under measurement;

a sampling member brought into proximity with a surface of said object under measurement and connected to the means for sucking in air and the discharging means of discharging a fluid; and blocking member made of a flexible material being provided at about the outer periphery of said sampling member, wherein said flexible material comprises a thin sheet attached along one edge of the sampling member.

4. A surface contamination measuring apparatus according to claim 3, wherein said flexible material comprises a single synthetic rubber sheet.

5. A surface contamination measuring apparatus according to claim 3, wherein said blocking member has one end connected to said sampling member in proximity to the outer periphery thereof, and another end remaining detached.

6. A surface contamination measuring apparatus according to claim 3, wherein said blocking member is disposed adjacent to the surface to be measured so that a low-pressure space is formed between said sampling member and said object under measurement.

7. A surface contamination measuring apparatus according to claim 3, wherein said sampling member has a plan-view shape that is circular.

8. A surface contamination measuring apparatus according to claim 3, wherein said sampling member has a plan-view shape that is rectangular.

9. A surface contamination measuring apparatus according to claim 3, wherein said sampling member has a plan-view shape that is triangular.

* * * * *